(12) United States Patent
Lin et al.

(10) Patent No.: US 10,034,844 B2
(45) Date of Patent: Jul. 31, 2018

(54) METHOD FOR ENHANCING IMMUNITY, INHIBITING ALLERGIC REACTION, AND/OR INHIBITING AUTOIMMUNE REACTION

(71) Applicant: TCI CO., LTD., Taipei (TW)

(72) Inventors: Yung-Hsiang Lin, Taipei (TW); I-Hui Chen, Taipei (TW); Hui-Hsin Shih, Taipei (TW); Yun-Ching Tsai, Taipei (TW); Qiao-Ting Chen, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 15/404,069

(22) Filed: Jan. 11, 2017

(65) Prior Publication Data
US 2017/0216230 A1 Aug. 3, 2017

Related U.S. Application Data

(60) Provisional application No. 62/288,261, filed on Jan. 28, 2016.

(51) Int. Cl.
*A61K 31/19* (2006.01)
(52) U.S. Cl.
CPC .................................. *A61K 31/19* (2013.01)
(58) Field of Classification Search
None
See application file for complete search history.

(56) References Cited

U.S. PATENT DOCUMENTS

2015/0110901 A1  4/2015  Chung et al.

OTHER PUBLICATIONS

Kawashima et al (JP200138739A), translation attached. 2013.*

* cited by examiner

*Primary Examiner* — Samantha L Shterengarts
(74) *Attorney, Agent, or Firm* — Christensen, Fonder, Dardi & Herbert PLLC

(57) ABSTRACT

A method for enhancing immunity, inhibiting allergic reaction, and/or inhibiting autoimmune reaction is provided. The method comprises administering to a subject in need an effective amount of a compound of formula (I):

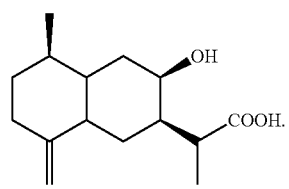

(I)

4 Claims, 3 Drawing Sheets

METHOD FOR ENHANCING IMMUNITY, INHIBITING ALLERGIC REACTION, AND/OR INHIBITING AUTOIMMUNE REACTION

CROSS REFERENCE TO RELATED APPLICATIONS

This application claims priority to U.S. Provisional Application Ser. No. 62/288,261 filed on Jan. 28, 2016, in the United States Patent and Trademark Office, the disclosures of which is incorporated herein in their entirety by reference.

FIELD OF THE INVENTION

The present invention relates to the use of a compound of formula (I):

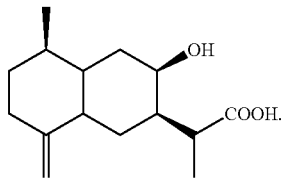

The present invention especially relates to the use of the compound of formula (I) to enhance immunity, inhibit allergic reaction, and/or inhibit autoimmune reaction.

BACKGROUND OF THE INVENTION

The immune system of an organism plays an important role in maintaining the health of the organism. There are a lot of immunocytes in an immune system. Under normal circumstances, immunocytes can serve appropriate immune functions, such as helping with the defense against external pathogens (e.g., bacteria, fungi, viruses, microorganisms, and various antigens) as well as degrading the aged and mal-functional cells or the abnormal cancer cells produced by gene mutation in the body. Therefore, an enhancement of immunity is helpful for organisms to stay healthy. The function of immunocytes decreases with aging, and this is one of the major causes of the decrease in immunity. Accordingly, if the aging of immunocytes can be delayed, the immunity can be effectively enhanced.

The dysfunction of immunocytes (also called immune system disorder), including hypoimmunity, allergic reaction, autoimmune reaction, etc., is harmful to the health of an organism. Specifically, a subject with hypoimmunity is susceptible to the infection of external pathogens, and a cancer may occur if the cancer cells in the subject are not cleaned promptly. An allergic reaction refers to the over-reaction of an immune system when it encounters foreign antigens, while an autoimmune reaction refers to an attack of immunocytes of the organisms on their own cells or organs. Therefore, if the immunity could be effectively enhanced and the allergic reaction and/or the autoimmune reaction could be effectively inhibited, the goal of improving the function of the immune system can be achieved to make a subject stay healthy.

In medicine, though it is known that appropriate exercise and diet as well as sufficient sleep can enhance the immunity of a subject, modern people are generally deficient in exercise and sleep and usually have a nutritional imbalanced diet. Therefore, it becomes impractical to achieve the goal of strengthening the immune system through exercise, sleep and diet. It is known that some medicines such as epinephrine, antihistamines, and steroids are effective in inhibiting allergic reactions and autoimmune reactions; however, the use of such medicines is usually accompanied by side effects such as palpitation, fremitus, and anxiety. Currently, other new therapeutic methods (such as desensitization therapy and biologics therapy) are available, though they are expensive and provide limited effects.

Given the above, there is still a need for a method that is effective in enhancing immunity, inhibiting allergic reaction, and/or inhibiting autoimmune reaction. Inventors of the present invention have found that the compound of formula (I) can effectively promote the activation of immunocytes, delay the aging of immunocytes, and inhibit the expressions of genes that induce allergic reaction and autoimmune reaction. Therefore, the use of the compound of formula (I) can achieve the effects of enhancing immunity, inhibiting allergic reaction, and/or inhibiting autoimmune reaction, while avoiding the side effects caused by medicines such as epinephrine, antihistamines, and steroids.

SUMMARY OF THE INVENTION

An objective of the present invention is to provide a use of the above compound of formula (I) in the manufacture of a medicament, wherein the medicament is for enhancing immunity, inhibiting allergic reaction, and/or inhibiting autoimmune reaction.

Another objective of the present invention is to provide a use of the above compound of formula (I) in the manufacture of a food, wherein the food is for enhancing immunity, inhibiting allergic reaction, and/or inhibiting autoimmune reaction; wherein the food is a health food or a nutritional supplement food. Preferably, the food is a health food.

Still another objective of the present invention is to provide a method of enhancing immunity, inhibiting allergic reaction, and/or inhibiting autoimmune reaction, comprising administering to a subject in need an effective amount of the above compound of formula (I).

The detailed technology and preferred embodiments implemented for the present invention are described in the following paragraphs accompanying the appended drawings for people skilled in this field to well appreciate the features of the claimed inventive.

DESCRIPTION OF THE PREFERRED EMBODIMENTS

Figure 1:
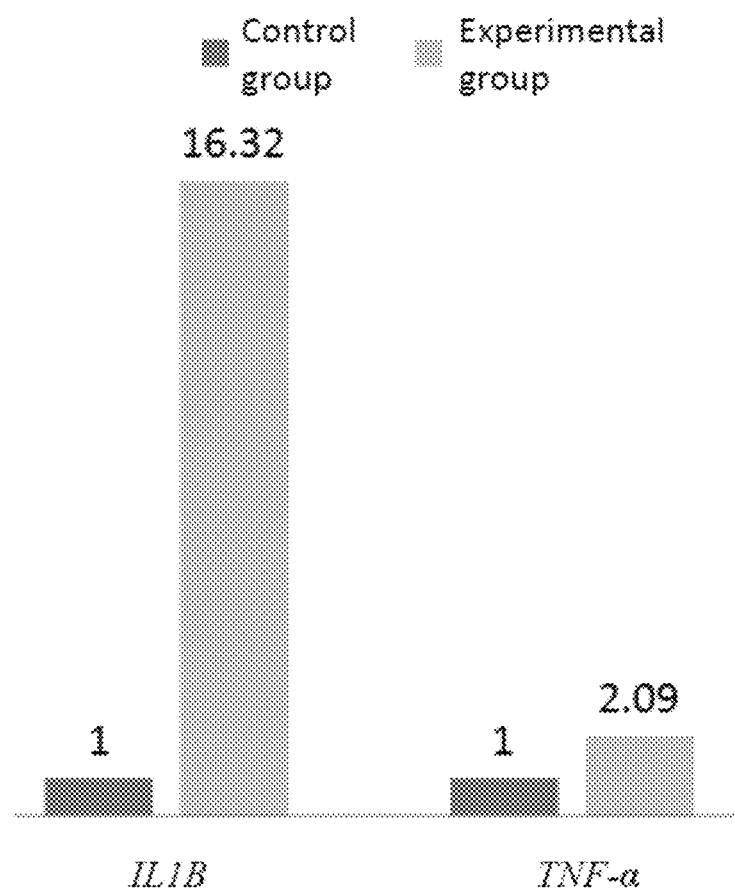
FIG. 1 illustrates the analysis results of an RNA microarray, showing the expression levels of IL-1B (interleukin 1 beta) and TNF-α (tumor necrosis factor alpha) in peripheral blood mononuclear cells (PBMCs) of the control group (i.e., the group cultured in a medium that was free of the compound of formula (I)) and the experimental group (i.e., the group cultured in a medium containing the compound of formula (I))

The following will describe some embodiments of the present invention in detail. However, without departing from the spirit of this invention, the present invention may be embodied in various embodiments and should not be illustrated as limited to the embodiments descried in the specification. In addition, unless otherwise indicated herein, the expressions "a," "an," "the," or the like recited in this specification (especially in the claims) are intended to include both the singular and plural forms.

As indicated above, the immune function plays an important role in maintaining the health of organisms. However, the medical industry to date is still deficient in effective methods for enhancing immunity and simultaneously inhibiting the occurrence of allergic reaction and/or autoimmune reaction. Inventors of the present invention found that the compound of formula (I) as follows can effectively promote the activation of immunocytes, delay the aging of immunocytes, and inhibit the expressions of genes inducing allergic reaction and/or autoimmune reaction, and thus, can be used to enhance immunity, inhibit allergic reaction, and/or inhibit autoimmune reaction:

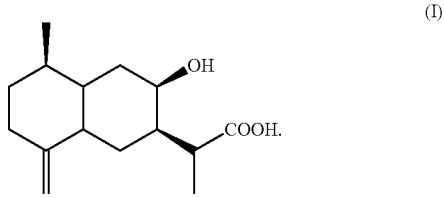 [SMILES: C=C1CC[C@@H](C)C2C[C@@H](O)[C@@H](C(C)C(=O)O)CC12]

(I)

Therefore, the present invention relates to a use of the compound of formula (I) in the manufacture of a medicament, wherein the medicament is for enhancing immunity, inhibiting allergic reaction, and/or inhibiting autoimmune reaction.

Depending on the desired administration manner, the medicament according to the present invention may be provided in any suitable form without particular limitations. For example, the medicament can be administered by an oral or parenteral (such as subcutaneous, intravenous, intramuscular, peritoneal, or nasal) route to a subject in need, but is not limited thereby. Depending on the form and purpose, suitable carriers can be chosen and used to provide the medicament, wherein the carriers include excipients, diluents, auxiliaries, stabilizers, absorbent retarders, disintegrants, hydrotropic agents, emulsifiers, antioxidants, adhesives, binders, tackifiers, dispersants, suspending agents, lubricants, hygroscopic agents, etc.

As a dosage form suitable for oral administration, the medicament provided by the present invention may comprise any pharmaceutically acceptable carrier that will not adversely affect the desired effects of the compound of formula (I). Examples of suitable carriers can include, for example, water, saline, dextrose, glycerol, ethanol or its analogs, cellulose, starch, sugar bentonite, or combinations thereof. The medicament can be provided in any suitable form for oral administration, such as in the form of a tablet (e.g., dragee), a pill, a capsule, a granule, a pulvis, a fluid extract, a solution, syrup, a suspension, a tincture, etc.

As for the form of injection or drip suitable for subcutaneous, intravenous, intramuscular, or peritoneal administration, the medicament provided by the present invention may comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the medicament as an intravenous infusion, an emulsified intravenous infusion, a powder for injection, a suspension for injection, or a powder suspension for injection, etc. Alternatively, the medicament may be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the medicament provided by the present invention may further comprise a suitable amount of additives, such as a flavoring agent, a toner, or a coloring agent for enhancing the palatability and the visual perception of the medicament, and/or a buffer, a conservative, a preservative, an antibacterial agent, or an antifungal agent for improving the stability and storability of the medicament. In addition, the medicament may optionally further comprise one or more other active ingredient(s) (such as epinephrine, antihistamines, steroids, etc.), or be used in combination with a medicament comprising one or more other active ingredients, to further enhance the effects of the medicament or to increase the application flexibility and adaptability of the preparation thus provided, as long as the other active ingredients will not adversely affect the desired effects of the compound of formula (I).

Depending on the desire, age, body weight, and health conditions of the subject, the medicament provided by the present invention may be dosed with various administration frequencies, such as once a day, multiple times a day, or once every few days, etc. For example, when the medicament is applied orally to a subject for enhancing immunity, inhibiting allergic reaction, and/or inhibiting autoimmune reaction, the dosage of the medicament is about 0.1 mg (as the compound of formula (I))/kg-body weight to about 10 mg (as the compound of formula (I))/kg-body weight per day, preferably about 1 mg (as the compound of formula (I))/kg-body weight to about 10 mg (as the compound of formula (I))/kg-body weight per day, and more preferably about 5 mg (as the compound of formula (I))/kg-body weight to about 10 mg (as the compound of formula (I))/kg-body weight per day, wherein the unit "mg/kg-body weight" refers to the dosage required per kg-body weight of the subject.

Optionally, the medicament provided by the present invention may be used in combination with desensitization therapy and/or biologics therapy to enhance immunity, inhibit allergic reaction and/or inhibit autoimmune reaction.

The present invention also relates to a use of the compound of formula (I) in the manufacture of a food product, wherein the food is for enhancing immunity, inhibiting allergic reaction, and/or inhibiting autoimmune reaction.

The food product according to the present invention could be a health food or a nutritional supplement food, and may be provided as dairy products, meat products, breadstuff, pasta, cookies, troche, fruit juices, teas, sport drinks, nutritional drinks, etc., but is not limited thereby. Preferably the food product according to the present invention is a health food.

Depending on the desire, age, body weight and healthy conditions of the subject, the health food and nutritional supplement food provided by the present invention can be taken in various frequencies, such as once a day, several times a day or once every few days, etc. The amount of the compound of formula (I) in the health food and nutritional supplement food provided by the present invention can be adjusted, preferably to the amount that it should be taken daily, depending on the specific population. For example, if the recommended daily dosage for a subject is about 10 mg and each serving of the health food contains 5 mg of the compound of formula (I), the subject can take about two servings of the health food per day.

The recommended daily dosage, use standards and use conditions for a specific population (e.g., pregnant woman, diabetic patients, and leukemia patients), or the recommendations for a use in combination with another food product or medicament can be indicated on the exterior package of the health food and/or nutritional supplement food provided by the present invention. Thus, it is favorable for the user to take the health food and/or the nutritional supplement food by him- or herself safely and securely without the instructions of a doctor, pharmacist, or related executive.

The compound of formula (I) used in the present invention can be provided in any suitable manner. For example, the compound of formula (I) can be purchased commercially, be purified and isolated from the extracts of plants, or be obtained by a chemical synthesis. For example, the compound of formula (I) can be obtained by the extraction and purification of *Saussurea involucrate* (the calluses are usually used).

The present invention further relates to a method of enhancing immunity, inhibiting allergic reactions, and/or inhibiting autoimmune reactions, comprising administering to a subject in need an effective amount of the compound of formula (I). In this method, the resource, applied route, applied form, suitable dosage and use of the compound of formula (I) are all in line with the above description about the medicament of the present invention.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Examples

A. Harvest of Peripheral Blood Mononuclear Cells (PBMCs)

PBMCs are immunocytes present in the peripheral blood. In these preparation examples, PBMCs were isolated from the peripheral blood obtained from healthy donors.

B. Treatments Applied to PBMCs (b1) 1 mL X-VIVO 10 medium was added into each well of a 24-well plate, and then PBMCs obtained from step A were seeded into the medium with a density of $1 \times 10^6$ to $2 \times 10^6$/well; and (b2) PBMCs obtained from step b1 were separated into two groups for the following treatments:

Control group: the PBMCs-containing medium was directly incubated in a 37° C. constant temperature incubator with 5% $CO_2$ (i.e., PBMCs were cultured in a medium that was free of the compound of formula (I)) for 24 hours;

Experimental group: the compound of formula (I) was added to the PBMCs-containing medium until a final concentration of 5%, and then the medium was incubated in a 37° C. constant temperature incubator with 5% $CO_2$ for 24 hours.

C. Detection of the Expression Level of mRNA (c1) Purification and Amplification of aRNA (c11) PBMCs treated by step b2 (including the control group and the experimental group) were harvested for the RNA extraction and purification as following the TRIzol® Reagent manufacturers' instruction, and then NanoDrop 1000 spectrophotometer was used to measure the ratios of OD260/OD280 and OD260/OD230;

(c12) 1 µg of RNA was used to synthesize the first strand cDNA through reverse transcription;

(c13) The first strand cDNA obtained from step c12 was used to synthesize the second strand cDNA, and then the double strand cDNA was purified;

(c14) The double strand cDNA obtained from step c13 was used to synthesize the amino Allyl-modified aRNA through the transcription, and then the aRNA was purified; and (c15) Cy5 fluorescent dye was used for performing the dye coupling reaction on the purified-aRNA, and then the dye-labeled aRNA was purified.

(c2) RNA Microarray (c21) The dye-labeled aRNA obtained from step c15 was hybridized to the Human Whole Genome OneArray® with Phalanx hybridization buffer and Phalanx Hybridization System;

(c22) After 16 hours of hybridization, non-specific binding targets were washed away;

(c23) The microarray was screened with a DNA Microarray Scanner (Model G2505C);

(c24) The Cy5 fluorescent intensities of each spot were analyzed with GenePix 4.1 software;

(c25) Steps c21 to c24 were repeated at least twice in each single sample with a reproducibility more than 0.975, and then the average values of signal intensities were loaded into the Rosetta Resolver System®;

(c26) The data of the control group and experimental group were compared, and a t-test was used to figure out the genes that significantly changed in the expression levels; and (c27) Genes that significantly changed in the expression levels were used to perform cluster analysis to figure out the affected pathway.

Example 1: Effect of Compound of Formula (I) on Enhancing Immunity (1-1) Activation of Macrophage Both interleukin-1 (IL-1) and TNF-α are pro-inflammatory cytokines and can persistently stimulate the activation of macrophages. Activated macrophages are capable of cleaning pathogens, and thus, can effectively reduce the harm caused by the pathogens.

To know whether the compound of formula (I) can promote the activation of macrophages, after determining mRNA expression levels via the above Preparation example C, the expression levels of genes relating to macrophage activation (including IL-1B and TNF-α) of the control and experimental group were recorded respectively. Thereafter, the gene expression levels of the experimental group were normalized by using that of the control group as a basis. The results are shown in FIG. 1.

As shown in FIG. 1, as compared to the control group, the expression levels of IL-1B and TNF-α in the experimental group both significantly increased. The expression level of IL-1B in the experimental group even increased to be 16.32 times the level of the control group. These results indicate that the compound of formula (I) can effectively promote the activation of macrophage, and thus can be used to enhance the immunity of an organism against the external pathogens.

(1-2) Activation of Major Histocompatibility Complex Class I Pathway (MHC-I Pathway)

MHC-I pathway performs the cytotoxic reaction on cells being infected by viruses or bacteria. Therefore, the activation of MHC-I pathway is helpful for enhancing the immunity of an organism against the external pathogens. It is known that the increase of the expression levels of CTSL, HSPA1B, and HSPA2 represents the activation of the MHC-I pathway.

To know whether the compound of formula (I) can promote the activation of the MHC-I pathway, after determining mRNA expression levels via the above Preparation example C, the expression levels of genes relating to MHC-I pathway (including CTSL, HSPA1B, and HSPA2) of the control and experimental group were recorded respectively. Thereafter, the gene expression levels of the experimental group were normalized by using that of the control group as a basis. The results are shown in FIG. 2.

Figure 2:
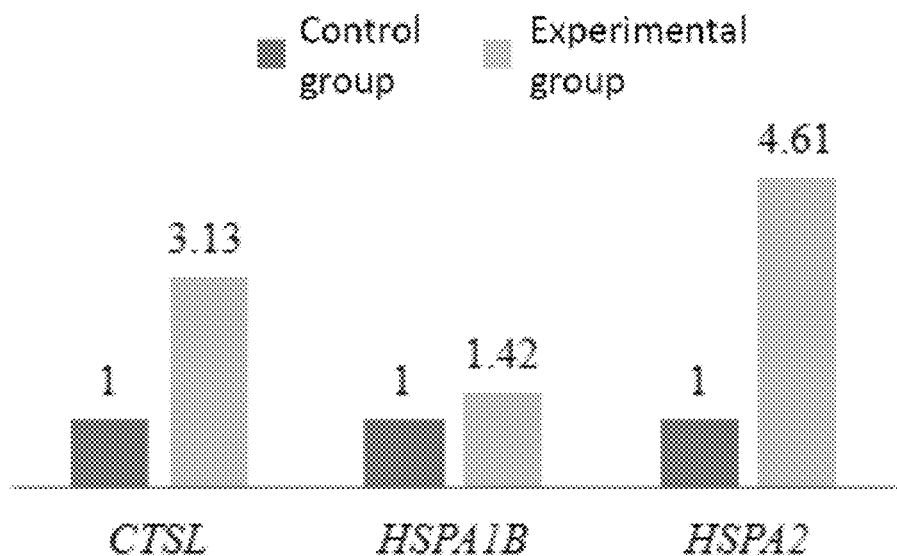
FIG. 2 illustrates the analysis results of an RNA microarray, showing the expression levels of CTSL (Cathepsin L), HSPA1B (heat shock protein family A member 1B), and HSPA2 (Heat Shock Protein Family A Member 2) in PBMCs of the control group and the experimental group.

As shown in FIG. 2, as compared to the control group, the expression levels of CTSL, HSPA1B, and HSPA2 in the experimental group all significantly increased. The expression levels of CTSL and HSPA2 in the experimental group even increased to be 3.13 and 4.61 times the level of the control group, respectively. These results indicate that the compound of formula (I) can effectively promote the activation of MHC-I pathway, and thus can be used to enhance the immunity of an organism against the external pathogens.

As shown in the results of 1-1 and 1-2, the compound of formula (I) can effectively enhance immunity.

Example 2: Effect of Compound of Formula (I) on Delaying the Aging of Immunocytes (2-1) Expression of Genes Delaying the Aging of Immunocytes It is known that genes such as FOXO3, SOD2, and TNFRSF14 are correlated with the anti-oxidation, proliferation, and growth of immunocytes. If the expression levels of those genes can be increased, the aging of immunocytes can be delayed, and thus, the immunocytes will stay at a young stage.

To know whether the compound of formula (I) can delay the aging of immunocytes, after determining mRNA expression levels via the above Preparation example C, the expression levels of genes helpful for delaying the aging of immunocytes (including FOXO3, SOD2, and TNFRSF14) of the control and experimental group were recorded respectively. Thereafter, the gene expression levels of the experimental group were normalized by using that of the control group as a basis. The results are shown in FIG. 3.

Figure 3:
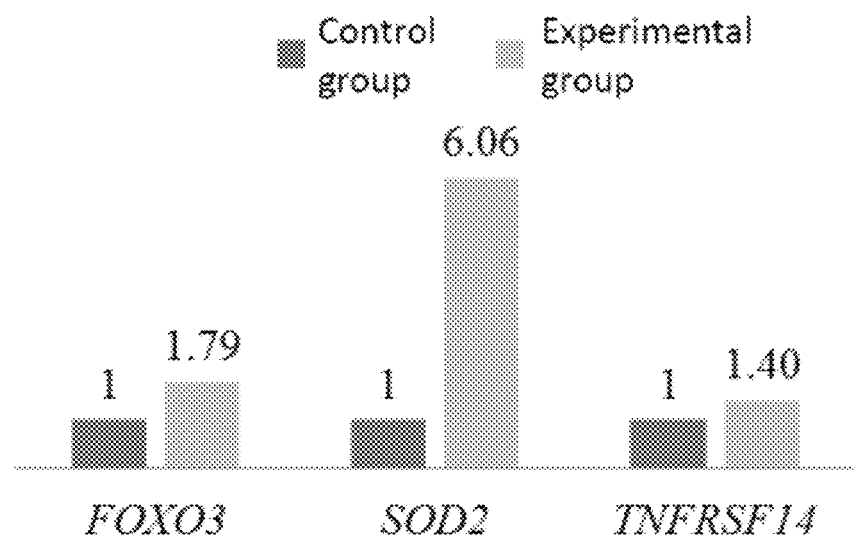
FIG. 3 illustrates the analysis results of an RNA microarray, showing the expression levels of FOXO3 (forkhead box O3), SOD2 (Superoxide dismutase 2), and TNFRSF14 (TNF superfamily, member 14) in PBMCs of the control group and the experimental group.

As shown in FIG. 3, as compared to the control group, the expression levels of FOXO3, SOD2, and TNFRSF14 in the experimental group all significantly increased. The expression level of SOD2 in the experimental group even increased to be 6.06 times the level of the control group. These results indicate that the compound of formula (I) can effectively delay the aging of immunocytes and make the immunocytes stay at the young stage.

(2-2) Expression of Aging Genes in Immunocytes

In immunocytes, there is another group of genes showing whether the immunocytes are at an old stage or not, and such genes include CD244, ITGA4, KLRG1, etc. The increment of the expression level of such genes represents that immunocytes have entered into an old stage.

To know whether the compound of formula (I) can delay the aging of immunocytes, after determining mRNA expression levels via the above Preparation example C, the expression levels of genes representing the old stage of immunocytes (including CD244, ITGA4, and KLRG1) of the control and experimental group were recorded respectively. Thereafter, the gene expression levels of experimental group were normalized by using that of the control group as a basis. The results are shown in FIG. 4.

Figure 4:
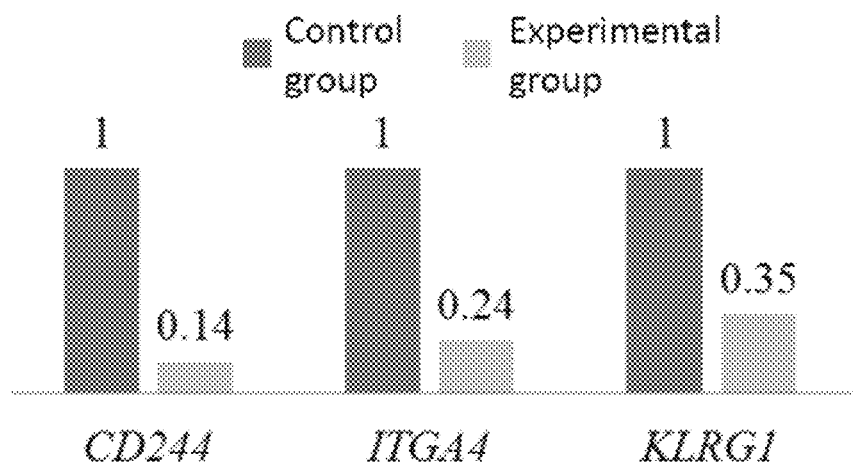
FIG. 4 illustrates the analysis results of an RNA microarray, showing the expression levels of CD244 (Cluster of Differentiation 244), ITGA4 (integrin subunit alpha 4), and KLRG1 (killer cell lectin-like receptor subfamily G, member 1) in PBMCs of the control group and the experimental group.

As shown in FIG. 4, as compared to the control group, the expression levels of CD244, ITGA4, and KLRG1 in the experimental group all significantly decreased. The expression levels of CD244, ITGA4, and KLRG1 in the experimental group decreased to be 0.14, 0.24, and 0.25 times the level of the control group, respectively. These results indicate that the compound of formula (I) can effectively prevent immunocytes from entering into the old stage, and thus can be used to delay the aging of immunocytes.

As shown in the results of 2-1 and 2-2, the compound of formula (I) can effectively delay the aging of immunocytes. As indicated above, the function of immunocytes decreases with aging, and this is one of the major causes of the decrease in immunity. Therefore, the results of 2-1 and 2-2 also indicate that the compound of formula (I) is effective in delaying the aging of immunocytes, and thus can be used to enhance immunity.

Example 3: The Effect of Compound of Formula (I) on Inhibiting Allergic Reaction It is known that the MHC-II pathway is highly associated with the occurrence of allergic reaction and/or autoimmune reaction. If the activation of the MHC-II pathway can be effectively inhibited, the allergic reaction and/or autoimmune reaction can be inhibited.

To know whether the compound of formula (I) can inhibit the activation of the MHC-II pathway, after determining mRNA expression levels via the above Preparation example C, the expression levels of genes relating to MHC-II pathway (including CD4, CD74, CIITA, HLA-DMB, HLA-DPA1, HLA-DPB1, HLA-DQB1, HLA-DRA, and LGMN) of the control and experimental group were recorded respectively. Thereafter, the gene expression levels of the experimental group were normalized by using that of the control group as a basis. The results are shown in FIG. 5.

Figure 5:
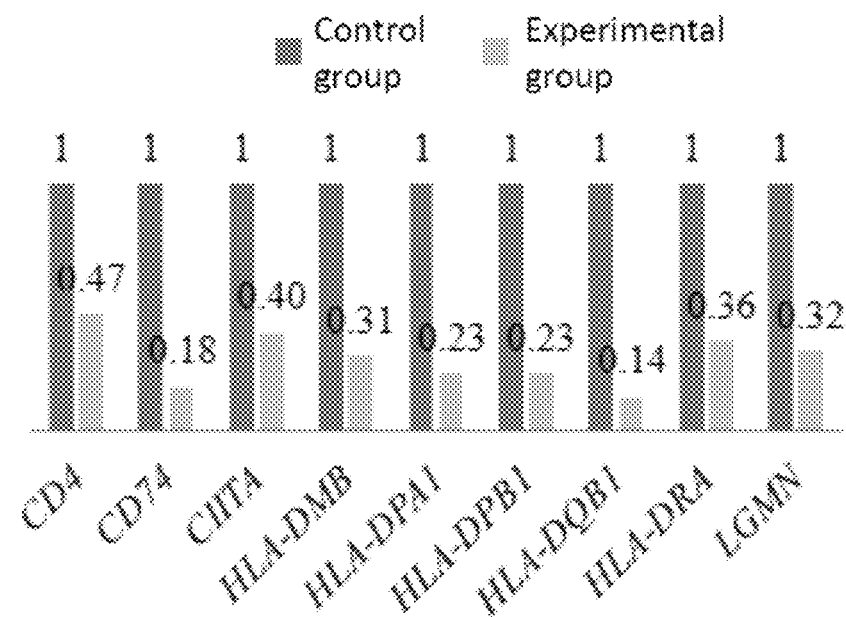
FIG. 5 illustrates the analysis results of an RNA microarray, showing the expression levels of CD4 (Cluster of Differentiation 4), CD74 (Cluster of Differentiation 74), CIITA (Class II Major Histocompatibility Complex Transactivator), HLA-DMB (human leukocyte antigen-DMB), HLA-DPA1, HLA-DPB1, HLA-DQB1, HLA-DRA, and LGMN (legumain) in PBMCs of the control group and the experimental group.

As shown in FIG. 5, as compared to the control group, the expression levels of CD4, CD74, CIITA, HLA-DMB, HLA-DPA1, HLA-DPB1, HLA-DQB1, HLA-DRA, and LGMN in the experimental group all significantly decreased. The expression levels of CD4, CD74, CIITA, HLA-DMB, HLA-DPA1, HLA-DPB1, HLA-DQB1, HLA-DRA, and LGMN in the experimental group decreased to be 0.47, 0.18, 0.40, 0.31, 0.23, 0.23, 0.14, 0.36, and 0.32 times the level of the control group, respectively. These results indicate that the compound of formula (I) can effectively inhibit the activation of MHC-II pathway, and thus can be used to inhibit allergic reaction and/or inhibit autoimmune reaction.

As shown in the above experiments, the compound of formula (I) of the present invention is effective in enhancing immunity, inhibiting allergic reaction, and/or inhibiting autoimmune reaction.

What is claimed is:

1. A method of enhancing immunity, inhibiting allergic reaction, and/or inhibiting autoimmune reaction, comprising administering to a subject suffering from the dysfunction of immunocytes an effective amount of a compound of formula (I):

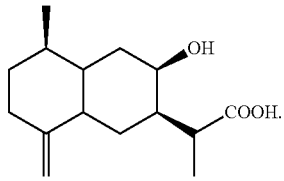

2. The method as claimed in claim 1, which is for enhancing immunity.

3. The method as claimed in claim 1, which is for inhibiting allergic reaction.

4. The method as claimed in claim 1, which is for inhibiting autoimmune reaction.

* * * * *